United States Patent [19]

Kai

[11] Patent Number: 4,627,968

[45] Date of Patent: Dec. 9, 1986

[54] SYNTHESIS OF CRYSTALLINE ALUMINOSILICATE WITH ALKYLUREA OR ALKYLTHIOUREA

[75] Inventor: Tadashi Kai, Machida, Japan

[73] Assignee: Asahi Kasei Kogyo Kabushiki Kaisha, Osaka, Japan

[21] Appl. No.: 774,454

[22] Filed: Sep. 10, 1985

[30] Foreign Application Priority Data

Sep. 10, 1984 [JP] Japan .................... 59-188165

[51] Int. Cl.[4] .................................. C10B 33/28
[52] U.S. Cl. .................................. 423/329; 423/328
[58] Field of Search ............... 423/328 T, 329

[56] References Cited

U.S. PATENT DOCUMENTS

| | | | |
|---|---|---|---|
| 3,702,886 | 11/1972 | Argauer et al. | 423/328 |
| 3,875,290 | 4/1975 | Gring | 423/328 |
| 3,948,760 | 4/1976 | Gring | 208/111 |
| 4,100,262 | 7/1978 | Pelrine | 423/328 T |
| 4,259,306 | 3/1981 | Pelrine | 423/328 T |
| 4,320,242 | 3/1982 | Onodera et al. | 208/111 |
| 4,462,971 | 7/1984 | Hinnenkamp et al. | 423/328 T |
| 4,472,366 | 9/1984 | Takahashi | 423/328 |
| 4,490,342 | 12/1984 | Valyocsik | 423/328 T |

OTHER PUBLICATIONS

Lok et al., "The Role of Organic Molecules in Molecular Sieve Synthesis", Zeolites, vol. 3, Oct., 1983, pp. 282–291.

"Zeolite Molecular Sieves", Structure Chemistry and Use, Donald W. Breck, pp. 304–313.

Primary Examiner—John Doll
Assistant Examiner—Lance Johnson
Attorney, Agent, or Firm—Birch, Stewart, Kolasch & Birch

[57] ABSTRACT

In the synthesis of a crystalline aluminosilicate by heating an aqueous mixture containing a silica source, an alumina source and an alkali metal source, at least one compound selected from lower alkylureas and lower alkylthioureas is permitted to co-exist with the mixture.

10 Claims, 6 Drawing Figures

2θ (DEGREE)

SYNTHESIS OF CRYSTALLINE ALUMINOSILICATE WITH ALKYLUREA OR ALKYLTHIOUREA

BACKGROUND OF THE INVENTION (1) Field of Industrial Application

This invention relates to a process for synthesizing a crystalline aluminosilicate, particularly a high silica crystalline aluminosilicate, useful as a catalyst, for example in industrial fields, such as chemistry, petroleum processing, and the like.

(2) Description of the Prior Art

In the synthesis of high silica crystalline aluminosilicate, there have been known processes in which various quaternary ammonium salts are used as the template (D. W. Breck, "Zeolite Molecular Sieves", p. 304–312, Wiley Interscience, 1974). Of these processes employing quaternary ammonium salts, particularly well known is the process in which a ZSM-5 type high silica crystalline aluminosilicate is synthesized with the use of tetrapropyl ammonium salt (U.S. Pat. No. 3,702,886). Recently, a process for synthesizing a high silica crystalline aluminosilicate by using an amide as the template has been disclosed (U.S. Pat. No. 4,472,366; Hiromi Nakamoto and Hiroshi Takahashi, Chemistry Letters, 169, 1981—The Chemical Society of Japan). According to such a process, a large amount of expensive reagents, such as tetrapropyl ammonium salt or N-hydroxyethyl lactamide is required to be used or, in the case of a reagent which is not necessarily expensive, such as an acetamide, a high silica crystalline aluminosilicate with a high catalyst activity can be synthesized, but with difficulty.

SUMMARY OF THE INVENTION

The present invention provides a process for synthesizing a crystalline aluminosilicate, which comprises heating an aqueous mixture containing a silica source, an alumina source and an alkali metal source in the presence of at least one compound selected from the group consisting of lower alkylureas and lower alkylthioureas. The composition of the crystalline aluminosilicate synthesized according to the process of the present invention, may be represented by $M_2O \cdot Al_2O_3 \cdot xSiO_2$ (wherein M is at least one of alkali metals and a hydrogen atom, and x is 10 to 1000), after washing with water and calcination.

According to the process of the present invention, a high silica crystalline aluminosilicate useful as highly active catalyst can be produced with a simple procedure and without the use of an expensive quaternary ammonium salt or amide compound. The high silica crystalline aluminosilicate obtained according to the process of the present invention is useful as a highly active catalyst for hydration of cycloolefins or olefins, synthesis of lower olefins or aromatic hydrocarbons from methanol, synthesis of aromatic hydrocarbons from paraffins or olefins, and so forth. It is possible to produce commercially a crystalline aluminosilicate, particularly a ZSM-5 type high silica crystalline aluminosilicate of high crystallinity, economically with the use of cheap starting materials.

Further, the process of the present invention enables the simple synthesis of a high silica crystalline aluminosilicate of fine grain and high crystallinity useful as highly active catalyst.

DESCRIPTION OF THE PREFERRED EMBODIMENTS

Figure 1:
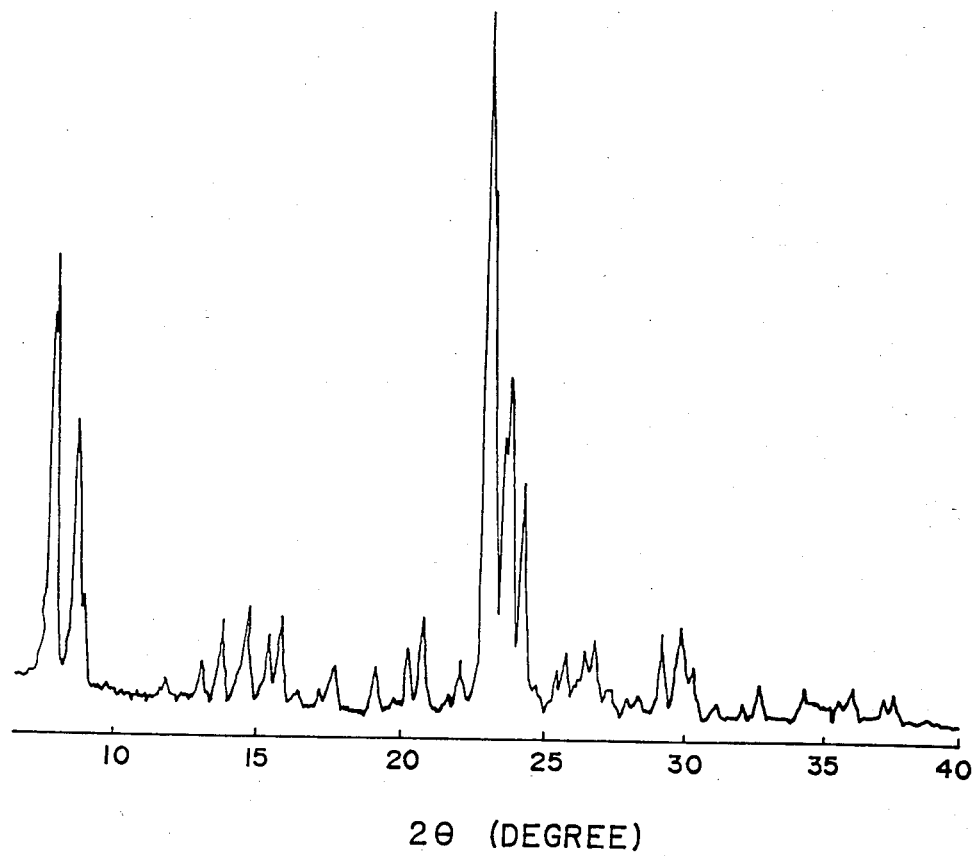
FIG. 1 is a X-ray diffraction pattern of a crystalline aluminosilicate synthesized in Example 1.

The silica source, the alumina source and the alkali metal source to be used in the present invention may be those generally employed in synthesis of zeolite (crystalline aluminosilicate). As the silica source, sodium silicate, water glass, silica gel, silicic acid anhydride, and the like may be used. As the alumina source, sodium aluminate, aluminum sulfate, aluminum nitrate, aluminum hydroxide, alumina, and the like may be used. As the alkali metal source, sodium hydroxide, sodium silicate, water glass, sodium aluminate, potassium hydroxide, and the like may be used. Preferably, sodium compounds may be used.

The lower alkylurea to be used in the present invention may be represented by the formula:

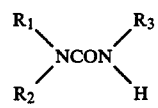

wherein one or two of $R_1$, $R_2$ and $R_3$ is an alkyl group having not more than 3 carbon atoms, with the remainder being hydrogen atom(s). Preferred examples of lower alkylurea may include methylurea, 1,3-dimethylurea, 1,1-dimethylurea, ethylurea, 1,1-diethylurea, 1,3-diethylurea, n-propylurea, isopropylurea, 1-methyl-1-ethylurea, 1-methyl-3-ethylurea and the like. Among them, dimethylurea is most preferred.

The lower alkylthiourea to be used in the present invention may be represented by the formula:

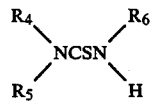

wherein one or two of $R_4$, $R_5$ and $R_6$ is an alkyl group having not more than 3 carbon atoms, with the remainder being hydrogen atom(s). Preferred examples of the lower alkylthiourea may include methylthiourea, 1,3-dimethylthiourea, 1,1-dimethylthiourea, ethylthiourea, 1,1-diethylthiourea, 1,3-diethylthiourea, n-propylthiourea, isopropylthiourea, 1-methyl-1-ethylthiourea, 1-methyl-3-ethylthiourea and the like.

The composition of the silica source, the alumina source, the alkali metal source, water and at least one compound selected from lower alkylureas and lower alkylthioureas may suitably fall within the range shown below, with the proviso that the silica source is calculated as gram mols of silica ($SiO_2$), the alumina source as gram mols of alumina ($Al_2O_3$), the alkali metal source as gram atoms of alkali metal, and water as gram mols:

silica source/alumina source = 10–1000;
water/silica source = 7–100;
alkali metal source/silica source = 0.05–10;
A/silica source = 0.01–1 wherein A represents the sum of gram mols of at least one compound selected from lower alkylureas and lower alkylthioureas.

If the silica source alumina source is less than 10, a high silica crystalline aluminosilicate can be synthesized only with difficulty, while at a ratio of silica source/alumina source over 1000, the crystalline aluminosilicate obtained will be lowered in catalytic activity.

If the water/silica source is less than 7, the synthetic operation, particularly on mixing, can be practiced with difficulty, and also a crystalline aluminosilicate will be formed only with difficulty. On the other hand, at a ratio of water/silica source over 100, a crystalline aluminosilicate can be obtained only with difficulty.

At a ratio of alkali metal source/silica source less than 0.05 or in excess of 10, a crystalline aluminosilicate can be synthesized only with difficulty.

If the A/silica source is less than 0.01, it is difficult to obtain a high silica crystalline aluminosilicate having high activity as a catalyst, while a ratio over 1 will make it difficult to synthesize a crystalline aluminosilicate at all.

A more preferable range of the composition is set forth below:

silica source/alumina source = 18–200;
water/silica source = 10–50;
alkali metal source/silica source = 0.05–1;
A/silica source = 0.05–0.7.

The most preferred range of the composition is as follows:

silica source/alumina source = 18–100;
water/silica source = 10–50;
alkali metal source/silica source = 0.15–1;
A/silica source = 0.05–0.3.

The aqueous composition containing a silica source, an alumina source and an alkali metal source in which at least one compound selected from lower alkylureas and lower alkylthioureas (hereinafter abbreviated as lower alkylureas) co-exist may be formulated as exemplified below. In water containing a silica source, water containing an alumina source and lower alkylureas are added and mixed therewith while stirring. If desired, the hydrogen ion concentration may be adjusted with the addition of an acid or an alkali. The preferable range of the hydrogen ion concentration pH is from 10 to 13. An alkali metal source may be added together with the silica source and/or the alumina source, or during adjustment of the hydrogen ion concentration. The above mentioned aqueous composition is maintained at an elevated temperature, preferably during stirring, until the formation of a crystalline aluminosilicate.

The heating temperature of the aqueous mixture may be 90° to 250° C., preferably 100° to 180° C., and more preferably 150° to 180° C. The pressure is not particularly limited, provided that the reaction system can maintain a liquid phase, but it is preferred to practice the reaction under a self-generating pressure of steam.

The period until the formation of crystalline aluminosilicate depends on the heating temperature and is not particularly limited, but it is generally preferred to be 10 to 47 hours.

In the process of the present invention, it is also possible to add a metal oxide source such as of vanadium, manganese, iron, zinc, gallium, boron, and the like, if desired, together with an alumina source or in place of the alumina source, to the aqueous mixture to synthesize a zeolite containing these foreign elements in a silicate network.

The crystalline aluminosilicate synthesized according to the process of the present invention can be subjected to ion-exchange with various cations according to the known method to prepare crystalline aluminosilicates containing various cations.

The aluminosilicate synthesized according to the process of the present invention can be molded into various shapes with or without the use of a known binder, if desired.

An X-ray diffraction pattern of the crystalline aluminosilicates synthesized according to the process of the present invention is shown in Table 1. It can be seen that they exhibit an X-ray diffraction patterns similar to that of ZSM-5 crystalline aluminosilicate zeolite.

TABLE 1

| Diffraction angle (2θ) (degree) | Relative intensity |
|---|---|
| 7.8 ± 0.2 | 50–90 |
| 8.7 ± 0.2 | 30–60 |
| 8.9 ± 0.2 | 10–30 |
| 23.0 ± 0.2 | 100 |
| 23.3 ± 0.2 | 60–90 |
| 23.6 ± 0.2 | 30–50 |
| 23.8 ± 0.2 | 40–70 |
| 24.4 ± 0.2 | 20–40 |

(X-ray source: CuKα)

The crystalline aluminosilicate synthesized according to the process of the present invention can be used preferably as the catalyst for various known reactions for which crystalline aluminosilicates can effectively be employed. Examples of various reactions, for which crystalline aluminosilicates can effectively be employed, may include hydration reactions of olefins or cycloolefins synthesis of lower olefins or aromatic hydrocarbons from methanol, synthesis of aromatic hydrocarbons from paraffins, olefins, and so forth. When crystalline aluminosilicates synthesized according to the process of the present invention are used as the catalyst, they are desirably employed under the state that their cation sites may substantially be occupied with protons.

The present invention is described in more detail by referring to the following Examples; however, it is not intended that these examples be limitative of the present invention.

EXAMPLE 1

Sodium silicate (water glass No. 3, 145 g) was mixed with 70 g of water (Liquid A). Aluminum sulfate [$Al_2(SO_4)_3.16H_2O$] (10.4 g) and 3.5 g of sulfuric acid were dissolved in 40 g of water (Liquid B). 1,3-Dimethylurea (17 g) was dissolved in 80 g of water (Liquid C). Liquid A was mixed with Liquid B and Liquid C with stirring by means of a homogenizer. The gel-like aqueous mixture obtained was charged into a 500 cc autoclave lined with polytetrafluoroethylene and heated at 160° C. under self-generating pressure with stirring at 900 rpm for 20 hours. The crystalline aluminosilicate formed was separated with a centrifuge, washed with water and dried at 120° C. for 4 hours.

The crystalline aluminosilicate obtained had a silica/alumina molar ratio of 28. The X-ray diffraction pattern of this product is shown in FIG. 1. It is similar to that of ZSM-5 zeolite.

The crystalline aluminosilicate synthesized was immersed in an aqueous ammonium chloride solution to be converted to the ammonium ion form crystalline aluminosilicate and, after drying, heated at 500° C. to be converted to the proton form crystalline aluminosilicate.

With the use of the proton form crystalline aluminosilicate prepared as mentioned above as catalyst, synthesis of 2-methyl-2-propanol by hydration of isobutene was carried out. That is, 30 g of isobutene, 50 g of water and 10 g of the catalyst were charged into a stainless steel autoclave of 150 ml inner volume previously replaced with nitrogen, and the autoclave was maintained with shaking in a water bath kept at 70° C. for 40 minutes. Then, the autoclave was taken out from the opened to evaporate isobutene. The remaining aqueous phase was analyzed by gas chromatography. The aqueous phase was found to contain 31.5% by weight of 2-methyl-2-propanol and no other product was detected.

EXAMPLE 2

Sodium silicate (water glass No. 3, 1,450 g) was mixed with 1,150 g of water (Liquid A); 125 g of aluminum sulfate [$Al_2(SO_4)_3 \cdot 16H_2O$] and 25 g of conc. sulfuric acid were dissolved in 600 g of water (Liquid B); further, 125 g of 1,3-dimethylurea was dissolved in 900 g of water (Liquid C). Liquid A was mixed with Liquid B and Liquid C with stirring by means of a homogenizer. The gel-like aqueous mixture obtained was charged into a stainless steel autoclave of a 5-liter inner volume and heated a 160° C. under self-generating pressure with stirring at 1200 rpm for 24 hours. The crystalline aluminosilicate formed was separated with a centrifugal machine, washed with water and dried at 120° C. for 4 hours.

Figure 2:
FIG. 2 is a scanning type electron microscope photograph of a crystalline aluminosilicate obtained in Example 2 (acceleration voltage 20 KV, magnification 50,000×)

The crystalline aluminosilicate obtained was subjected to measurements by an electron probe microanalyzer and X-ray diffraction. FIG. 2 shows a scanning type electron microscope photograph of the aluminosilicate obtained and shorter diameters of 0.4 to 0.6μ, having a silica/alumina molar ratio of 25, exhibiting the same X-ray diffraction pattern as in FIG. 1.

The yield measured after calcination at 550° C. for 5 hours was found to be about 90% based on the silicon charged (calculated as silicon dioxide).

The crystalline aluminosilicate obtained was calcined under air stream at 550° C. for 5 hours. Then, it was subjected to ion-exchange with an aqueous 2 mol/liter ammonium chloride solution, washed with water, filtered and dried, followed by calcining at 400° C. for 2 hours to convert the cation site to the proton form.

The proton form crystalline aluminosilicate (1 g), 2.4 g of cyclohexene and 2.7 g of water were charged into a pressure resistant glass ampoule of 15 ml inner volume, and the ampoule was maintained with shaking in an oil bath at 120° C. for one hour. The oil phase of the product was analyzed by gas chromatogrphy to find that 14.5 wt. % of cyclohexanol was contained therein.

EXAMPLE 3

Sodium silicate (water glass No. 3, 72 g) was mixed with 35 g of water (Liquid A). Aluminum sulfate [$Al_2(SO_4)_3 \cdot 16H_2O$] (5.2 g) and 1.2 g of sulfuric acid were dissolved in 20 g of water (Liquid B). 1,3-Diethylurea (11.4 g) was dissolved in 40 g of water (Liquid C). Liquid A was mixed with Liquid B and Liquid C with stirring by means of a homogenizer. The gel-like aqueous mixture obtained was charged into a 200 cc autoclave lined with polytetrafluoroethylene and heated at 160° C. under self-generating pressure with stirring at 800 rpm for 20 hours.

Figure 3:
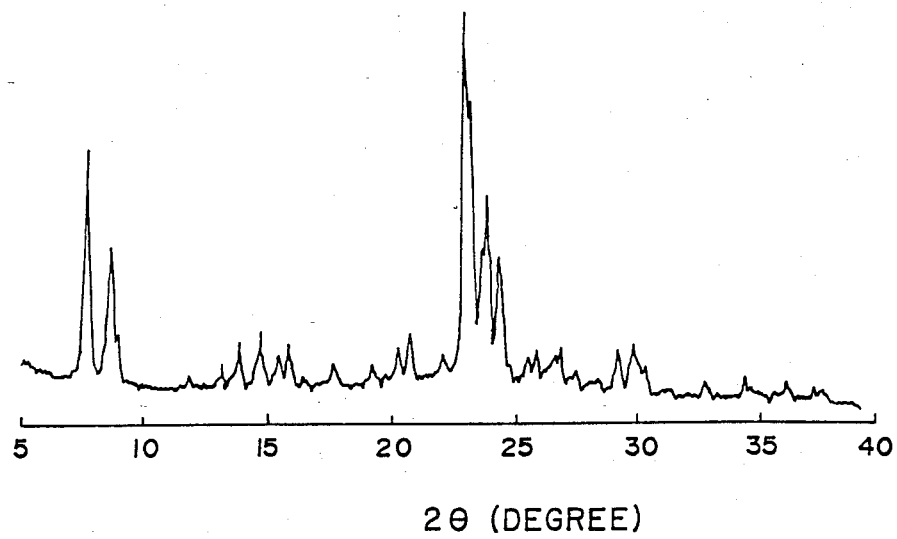
FIG. 3 is a X-ray diffraction chart of a crystalline aluminosilicate synthesized in Example 3.

The crystalline aluminosilicate obtained was treated similarly as in Example 1 to obtain 18.2 g of a crystalline aluminosilicate, which was found to have a silica/alumina molar ratio of 29. The X-ray diffraction pattern of this product is shown in FIG. 3, which is similar to that of ZSM-5 zeolite.

EXAMPLE 4

Figure 4:
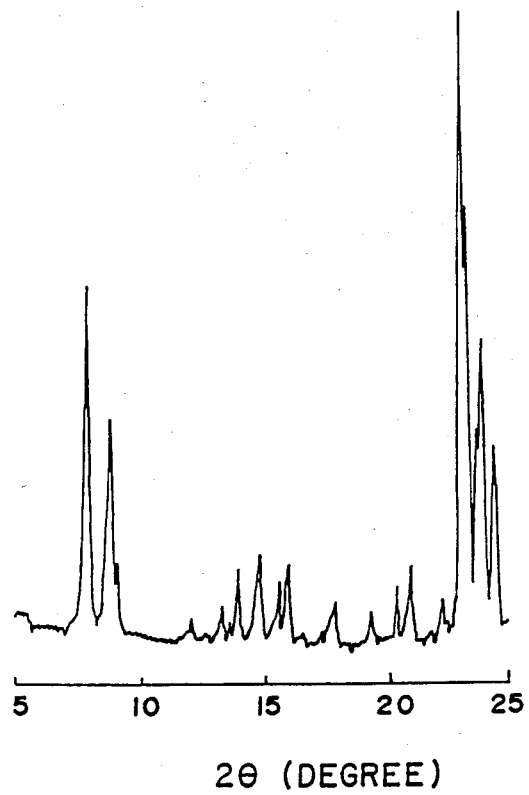
FIG. 4 is a X-ray diffraction chart of a crystalline aluminosilicate synthesized in Example 4.

Sodium silicate (water glass No. 3, 145 g) was mixed with 70 g of water (Liquid A). Aluminum sulfate [$Al_2(SO_4)_3 \cdot 16H_2O$] (10.4 g) and 2 g of sulfuric acid were dissolved in 40 g of water (Liquid B). 1,3-Dimethylthiourea (17 g) was added in 80 g of water (Liquid C). Liquid A was mixed with Liquid B and Liquid C with vigorous stirring. The gel-like aqueous mixture obtained was heated at 160° C. with stirring at 900 rpm for 24 hours. The crystalline aluminosilicate formed was separated with a centrifuge, washed with water and dried at 120° C. The crystalline aluminosilicate obtained exhibited an X-ray diffraction pattern shown in FIG. 4, which is similar to that of ZSM-5 zeolite.

EXAMPLE 5

Figure 5:
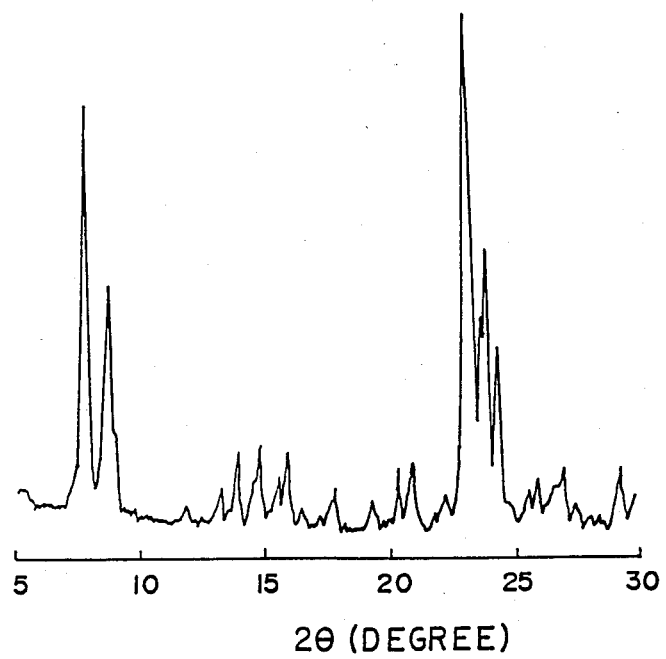
FIG. 5 is a X-ray diffraction chart of a crystalline aluminosilicate synthesized in Example 5.

Sodium silicate (water glass No. 3, 36 g) was mixed with 20 g of water (Liquid A). Aluminum sulphate [$Al_2(SO_4)_3 \cdot 16H_2O$] (1.3 g), 5.0 g of methylurea and 0.7 g of sulfuric acid were dissolved in 30 g of water (Liquid B). Liquid A was mixed with Liquid B with stirring to obtain a gel-like aqueous mixture. The aqueous mixture was charged into a 100 ml micro-cylinder lined with polytetrafluoroethylene, and maintained at 170° C. under self-generating pressure for 47 hours. The crystalline aluminosilicate was recovered and treated similarly as in Example 1. The crystalline aluminosilicate obtained was found to have a silica/alumina molar ratio of 47. The X-ray diffraction pattern of this product is shown in FIG. 5, which is similar to that of ZSM-5 zeolite.

EXAMPLE 6

Figure 6:
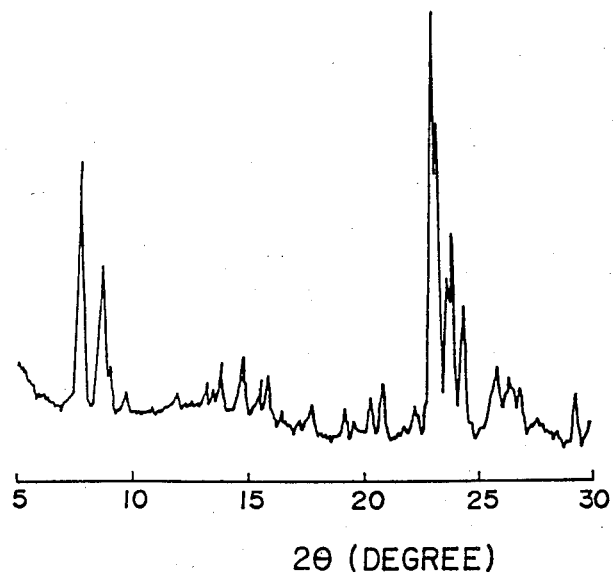
FIG. 6 is a X-ray diffraction chart of a crystalline aluminosilicate synthesized in Example 6.

Example 5 was repeated except that 5.0 g of ethylurea was employed in place of 5.0 g of methylurea to obtain crystalline aluminosilicate. The crystalline aluminosilicate obtained was found to be shaped in hexagonal plates with a silica/alumina molar ratio of 45. Its X-ray diffraction pattern is shown in FIG. 6. It is similar to the X-ray diffraction pattern of ZSM-5 zeolite.

EXAMPLE 7

Sodium silicate (water glass No. 3, 1,450 g) was mixed with 1,150 g of water (Liquid A); 74 g of aluminum sulfate [$Al_2(SO_4)_3 \cdot 16H_2O$] was dissolved in 600 g of water (Liquid B); further, 125 g of 1,3-dimethylurea was dissolved in 900 g of water (Liquid C). Liquid A was mixed with Liquid B and Liquid C with stirring by means of a homogenizer, and the hydrogen ion concentration (pH) in the mixture was adjusted by 12.5 by dropwise addition of 20% sulfuric acid. The gel-like aqueous mixture obtained was charged into a 5-liter autoclave and heated at 160° C. under self-generating pressure with stirring at 900 rpm for 24 hours. The crystalline aluminosilicate formed was separated with a centrifuge, washed with water and dried at 120° C. for 4 hours. The crystalline aluminosilicate obtained was subjected to measurements by an electron probe microanalyzer and X-ray diffraction. The aluminosilicate was found to be a five grain, having a silica/alumina molar ratio of 40 and show the X-ray pattern similar to that ZSM-5. The yield measured after calcining at 550° C. for 5 hours was found to be about 90% based on the silica in the starting material.

EXAMPLE 8

A gel-like aqueous mixture was prepared in the same manner as in Example 7, except for using 185 g of aluminum sulfate $[Al_2(SO_4)_3.16H_2O]$. The aqueous mixture was charged into a 5-liter autoclave and heated at 160° C. under self-generating pressure with stirring at 1000 rpm for 20 hours. The crystalline aluminosilicate formed was separated with a centrifuge, washed with water and dried at 120° C. for 4 hours. As the result of measurements by an electron probe microanalyzer and X-ray diffraction, the crystalline aluminosilicate was found to be similar to ZSM-5 in X-ray diffraction pattern, shaped in hexagonal plates with thicknesses of 0.4 to 0.6μ and shorter diameters of 0.4 to 0.6μ, having a silica/alumina molar ratio of 19. The yield measured after calcining at 550° C. for 5 hours was found to be about 90% based on the silica in the starting material.

EXAMPLE 9

Sodium silicate (water glass No. 3, 580 g) was mixed with 460 g of water (Liquid A); 75 g of aluminum sulfate $[Al_2(SO_4)_2.16H_2O]$ and 1.8 g of sulfuric acid were dissolved in 250 g of water (Liquid B); and 24.6 g of 1,3-dimethylurea was dissolved in 350 g of water (Liquid C). Liquid A was mixed with Liquid B and Liquid C with stirring by means of a homogenizer. Of the gel-like aqueous mixture obtained, 800 g was charged into a 1-liter autoclave and heated at 160° C. under self-generating pressure with stirring at 800 rpm for 22 hours. The crystalline aluminosilicate formed was separated with centrifuge, washed with water and dried at 120° C. for 4 hours. As the result of measurements by an electron probe microanalyzer and X-ray diffraction, the crystalline aluminosilicate was found to be similar to ZSM-5 in X-ray diffraction pattern, shaped in plates with shorter diameter of 0.2μ, having a silica/alumina ratio (molar ratio) of 19. The yield measured after calcining at 550° C. for 5 hours was found to be about 90% based on the silica in the starting material.

EXAMPLE 10

A gel-like aqueous mixture was prepared with the use of the same amounts of starting materials and according to the same procedure as in Example 9, except for changing the amount of 1,3-dimethylurea to 12.3 g. The gel-like aqueous mixture (800 g) was charged into an autoclave at 160° C. under self-generating pressure with stirring at 1000 rpm for 24 hours. The crystalline aluminosilicate formed was separated with centrifuge, washed with water and dried at 120° C. for 4 hours. As the result of measurements by an electron probe microanalyzer and X-ray diffraction, the crystalline aluminosilicate was found to be similar to ZSM-5 in X-ray diffraction pattern, shaped in plates with shorter diameter of 0.4μ, having a silica/alumina molar ratio of 19. The yield measured after heating at 550° C. for 5 hours was found to be about 90% based on silica in the starting material.

EXAMPLE 11

A solution of 580 g of sodium silicate (water glass No. 3) in 400 g of water and a solution of 45 g of aluminum sulfate $[Al_2(SO_4)_3.16H_2O]$, 46.8 g of dimethylurea, 25.5 g of sulfuric acid in 354 g of water was mixed with a homogenizer to obtain a gel-like aqueous mixture. The aqueous mixture (800 g) was charged into an autoclave and maintained at 170° C. under self-generating pressure with stirring at 1200 rpm for 40 hours. The crystalline aluminosilicate formed was separated with centrifuge, washed with water and dried at 120° C. for 4 hours. As the result of measurements by an electron probe microanalyzer and X-ray diffraction, the crystalline aluminosilicate was found to be similar to ZSM-5 in X-ray diffraction pattern, shaped in five grain, having a silica/alumina molar ratio of 26.

EXAMPLE 12

Sodium silicate (water glass No. 3, 580 g) was mixed with 460 g of water (Liquid A); 74.8 g of aluminum sulfate $[Al_2(SO_4)_3.16H_2O]$ and 1.8 g of sulfuric acid were dissolved in 300 g of water (Liquid B); and 66.4 g of 1,3-dimethylurea was dissolved in 300 g of water (Liquid C). Liquid A was mixed with Liquid B and Liquid C in the same manner as in Example 9. Of the gel-like aqueous mixture obtained, 800 g was charged into an autoclave and heated at 160° C. under self-generating pressure with stirring at 1000 rpm for 43 hours. The crystalline aluminosilicate formed was separated with a centrifuge, washed with water and dried at 120° C. for 4 hours. As the result of measurements by an electron probe microanalyzer and X-ray diffraction, the crystalline aluminosilicate was found to be similar to ZSM-5 in X-ray diffraction pattern, shaped in fine grain, having a silica/alumina molar ratio of 19.

EXAMPLE 13

Sodium silicate (water glass No. 3, 580 g) was mixed with 460 g of water (Liquid A); 74.8 g of aluminum sulfate $[Al_2(SO_4)_2.16H_2O]$ and 1.8 g of sulfuric acid were dissolved in 300 g of water (Liquid B); and 165.5 g of 1,3-dimethylurea was dissolved in 300 g of water (Liquid C). Liquid A was mixed with Liquid B and Liquid C in the same manner as in Example 9. Of the gel-like aqueous mixture obtained, 800 g was charged into a 1-liter autoclave and heated at 195° C. under self-generating pressure with stirring at 1000 rpm for 46 hours. The crystalline aluminosilicate formed was separated with a centrifuge, washed with water and dried at 120° C. for 4 hours. As the result of measurements by an electron probe microanalyzer and X-ray diffraction, the crystalline aluminosilicate was found to be similar to ZSM-5 in X-ray diffraction pattern.

COMPARATIVE EXAMPLE 1

Water glass No. 3 (72.5 g) was dissolved in 63 g of water (Liquid A). Sulfuric acid (1.41 g) and 5.28 g of aluminum sulfate $[Al_2(SO_4)_2.18H_2O]$ were dissolved in 20 g of water (Liquid B). Acetamide (4.50 g) was dissolved in 10 g of water (Liquid C). Liquid A was charged into a 500 ml stainless steel autoclave coated with tetrafluoroethylene polymer and, while stirring the liquid (A), Liquid C was added, followed by addition of Liquid B. The mixture was maintained in this autoclave at 150° C. with stirring at 300 rpm for 7 days.

The crystals were separated by filtration from the product taken out from the autoclave, washed with water and dried at 110° C. for 16 hours. The crystals were then calcined at 540° C. for 24 hours. The operation of ion-exchange of 5 g of the crystalline aluminosilicate with 75 ml of an aqueous 5 mol/liter ammonium chloride solution at 100° C. was repeated three times. Then, the aluminosilicate was washed completely until no chloride ion was recognized, dried at 110° C. for 16 hours and heated at 540° C. in the air for one day. The proton form crystalline aluminosilicate obtained was employed to carry out hydration reaction of cyclohexane according to the same procedure and under the same conditions as in Example 2. The oil phase in the product was found to contain 4.9 wt. % of cyclohexanol.

The invention having been thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A process for synthesizing a crystalline aluminosilicate, which comprises heating an aqueous mixture containing a silica source, an alumina source and an alkali metal source in the presence of at least one compound selected from the group consisting of lower alkylureas and lower alkylthioureas.

2. A process according to claim 1, wherein the aqueous mixture has a composition within the range as shown:
   silica source/alumina source = 10–1000;
   water/silica source = 7–100;
   alkali metal source/silica source = 0.05–10; and
   A/silica source = 0.01–1
wherein the silica source is calculated as gram mols of silica ($SiO_2$), alumina source as gram mols of alumina ($Al_2O_3$), alkali metal source as gram atoms of alkali metal, water as gram mols, and A represents the sum of gram mols of at least one compound selected from lower alkylureas and lower alkylthioureas.

3. A process according to claim 2, wherein the aqueous mixture has a composition within the range as shown:
   silica source/alumina source = 18–200;
   water/silica source = 10–50;
   alkali metal source/silica source = 0.05–1; and
   A/silica source = 0.05–0.7.

4. A process according to claim 2, wherein the aqueous mixture has a composition within the range as shown:
   silica source/alumina source = 18–100;
   water/silica source = 10–50;
   alkali metal source/silica source = 0.15–1; and
   A/silica source = 0.05–0.3.

5. A process according to claim 1, wherein the lower alkylureas are represented by the formula:

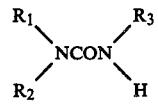

wherein one or two of $R_1$, $R_2$ and $R_3$ is an alkyl group having not more than 3 carbon atoms, with the remainder being hydrogen atom(s).

6. A process according to claim 1, wherein the lower alkylureas are selected from methylurea, 1,3-dimethylurea, 1,1-dimethylurea, ethylurea, 1,1-diethylurea, 1,3-diethylurea, n-propylurea, isopropylurea, 1-methyl-1-ethylurea and 1-methyl-3-ethylurea.

7. A process according to claim 1, wherein the lower alkylurea is dimethylurea.

8. A process according to claim 1, wherein the lower alkylthioureas are represented by the formula:

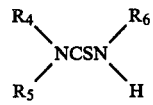

wherein one or two of $R_4$, $R_5$ and $R_6$ is alkyl group having not more than 3 carbon atoms, with the remainder being hydrogen atom(s).

9. A process according to claim 1, wherein the lower alkylthiourea is selected from methylthiourea, 1,3-dimethylthiourea, 1,1-dimethylthiourea, ethylthiourea, 1,1-diethylthiourea, 1,3-diethylthiourea, n-propylthiourea, isopropylthiourea, 1-methyl-1-ethylthiourea and 1-methyl-3-ethylthiourea.

10. A process according to claim 1, wherein the heating is carried out at 90° to 250° C. under self-generating pressure of steam for 10 to 47 hours.

* * * * *